(12) United States Patent
David et al.

(10) Patent No.: US 7,680,241 B2
(45) Date of Patent: Mar. 16, 2010

(54) MULTI-TUBE IMAGING SYSTEM SCATTER CORRECTION

(75) Inventors: Bernd David, Huettblek (DE); Michael Grass, Hamburg (DE); Astrid Fatou Lewalter, Aachen (DE); Rainer Pietig, Herzogenrath (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/305,458

(22) PCT Filed: Jun. 13, 2007

(86) PCT No.: PCT/US2007/071095

§ 371 (c)(1),
(2), (4) Date: Dec. 18, 2008

(87) PCT Pub. No.: WO2007/149749

PCT Pub. Date: Dec. 27, 2007

(65) Prior Publication Data

US 2009/0279659 A1  Nov. 12, 2009

Related U.S. Application Data

(60) Provisional application No. 60/805,518, filed on Jun. 22, 2006.

(51) Int. Cl.
*A61B 6/00* (2006.01)
(52) U.S. Cl. .............................................. 378/7; 378/9

(58) Field of Classification Search ............... 378/4–20; 600/428
See application file for complete search history.

(56) References Cited

U.S. PATENT DOCUMENTS

| 6,421,412 | B1 | 7/2002 | Hsieh et al. |
| 6,876,719 | B2 | 4/2005 | Ozaki |
| 2004/0079232 | A1 | 4/2004 | Groh et al. |
| 2004/0114710 | A1 | 6/2004 | Ozaki |
| 2004/0213371 | A1 | 10/2004 | Bruder et al. |
| 2006/0245545 | A1 | 11/2006 | Gunzler et al. |

FOREIGN PATENT DOCUMENTS

WO  03058222 A2  7/2003

*Primary Examiner*—Courtney Thomas

(57) ABSTRACT

A computed tomography reconstruction method includes concurrently emitting radiation from at least two x-ray sources (14), switching the output state of each of the at least two x-ray sources (14) within a plurality of respective cross scatter sampling intervals (50, 52, 54, 56) and detecting with a corresponding one of the sets of detectors (24) cross scatter radiation emitted by the other at least two x-ray sources (14), wherein the cross scatter sampling intervals are angularly spaced over a plurality of frames to allow the at least two x-ray sources (14) to concurrently emit radiation throughout at least one frame, deriving scatter correction data for each set of detectors (24) from corresponding cross scatter samples, scatter correcting the projection data with corresponding scatter correction data, and reconstructing the scatter corrected projection data to generate at least one image.

28 Claims, 2 Drawing Sheets

MULTI-TUBE IMAGING SYSTEM SCATTER CORRECTION

CROSS REFERENCE TO RELATED APPLICATIONS

This application claims the benefit of U.S. provisional application Ser. No. 60/805,518 filed Jun. 22, 2006, which is incorporated herein by reference.

The present application relates to medical imaging systems. It finds particular application to computed tomography (CT) and, more particularly to multi-tube imaging system scatter correction techniques.

The x-ray tubes in a conventional multi-tube CT imaging system can be concurrently driven such that both tubes simultaneously emit radiation through an imaging region. When concurrently driving the tubes as such, the imaging system can provide greater temporal resolution and faster data acquisition relative to a single tube system. For example, a system with two tubes that are angularly displaced about 90 degrees from each other along the rotation axis can acquire the same data as a single tube system in about half the time. In another example, using such system for cardiac CT, data acquisition over a fraction of a 180 degree gantry angle detects enough data for a 180 degree reconstruction. However, since the tubes are simultaneously emitting radiation, each detector detects primary and cross scatter radiation. Cross scatter radiation can severely deteriorate the signal-to-noise ratio and introduce artifact into the reconstructed images, and conventional anti-scatter grids do not suitably reduce cross scatter radiation.

One approach to mitigating cross scatter is to alternately drive the tubes such that only one tube emits radiation at any given time. However, this results in inefficient tube use (e.g., about 50% with a dual tube system), decreased temporal resolution, and a reduction in the number of photons detected (e.g., about halved with a dual tube system). Tube power may have to be increased beyond technological limits of conventional high power tubes to overcome the photon reduction. Another approach includes scatter correcting the data. For example, during each view or frame at least one tube can be turned "off." Cross scatter data can then be detected with detectors paired with the de-active tube. The cross scatter data can then be used to scatter correct projection data detected with these detectors. Such system is described in U.S. Pat. No. 6,876,719 to Ozaki; however with this system, tube efficiency and statistics are still degraded since at least one tube is not emitting radiation during a period within each view.

Present aspects of the application provide a new and improved cross scatter correction technique that addresses the above-referenced problems and others.

In accordance with one aspect, a computed tomography reconstruction method comprises concurrently emitting radiation from at least two x-ray sources rotating about an imaging region through the imaging region and detecting with corresponding sets of detectors projection data, which includes primary radiation emitted by a corresponding one of the at least two x-ray sources and cross scatter radiation emitted by the other of the at least two x-ray sources. The method further includes switching the output state of each of the at least two x-ray sources within a plurality of respective cross scatter sampling intervals and detecting with a corresponding one of the sets of detectors cross scatter radiation emitted by the other of the at least two x-ray sources, wherein the cross scatter sampling intervals are angularly spaced over a plurality of frames to allow the at least two x-ray sources to concurrently emit radiation throughout at least one frame.

The method further includes deriving scatter correction data for each set of detectors from corresponding cross scatter samples, scatter correcting the projection data with corresponding scatter correction data, and reconstructing the scatter corrected projection data to generate at least one image.

The invention may take form in various components and arrangements of components, and in various steps and arrangements of steps. The drawings are only for purposes of illustrating the preferred embodiments and are not to be construed as limiting the invention.

Figure 1:
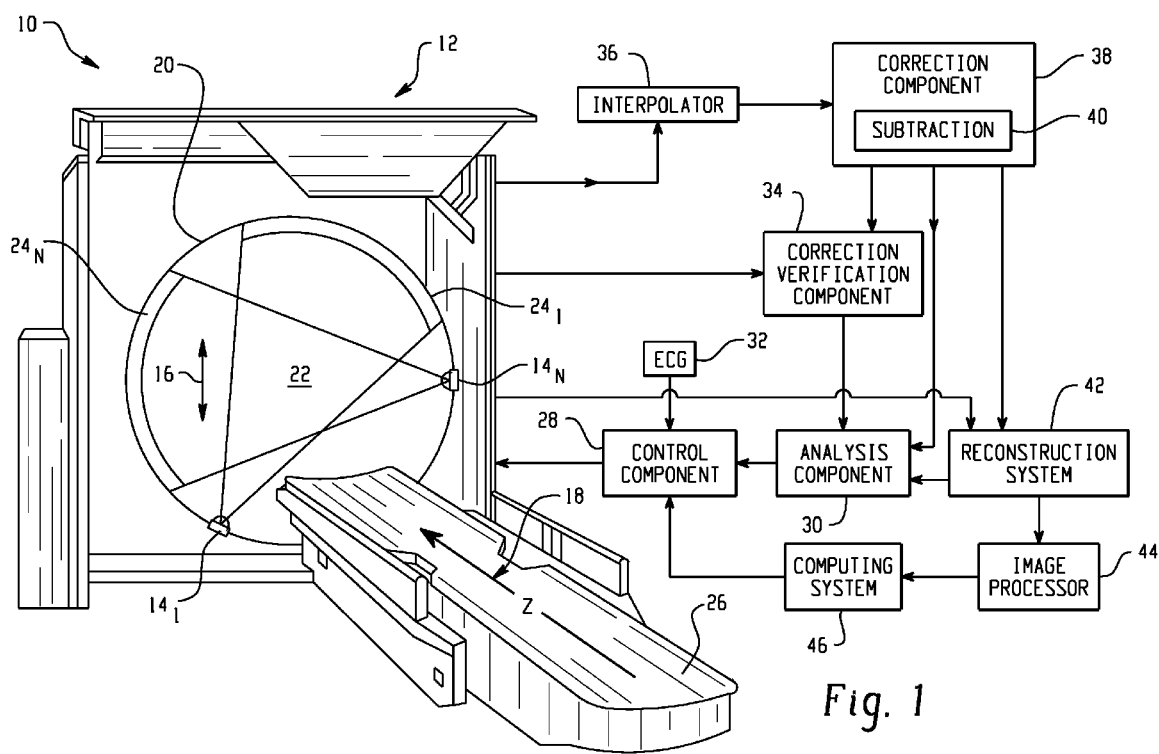
FIG. 1 illustrates a multi-source medical imaging system that periodically samples cross scatter radiation over data acquisition frames and derives scatter correction signals, from the cross scatter samples, for scatter correcting projection data.

With reference to FIG. 1, a medical imaging system 10 is illustrated. The medical imaging system 10 includes multiple x-ray sources that irradiate a subject and detectors that detect projection radiation. When the x-ray sources are concurrently emitting radiation, the projection data includes both primary and cross scatter radiation. The projection data is subsequently processed to remove the cross scatter radiation contributions, and the scatter corrected data is reconstructed to form one or more images. In one instance, the cross scatter contributions are removed from the projection data with a scatter correction signal. Such scatter correction signal can be created by periodically sampling only cross scatter (no primary) radiation with one or more detectors over a plurality of frames in which data is collected as the x-ray sources rotate through a data acquisition cycle and generating a scatter correction signal from these samples. The angular sampling (or frame) increment between cross scatter samples can be determined based on an angular frequency of the cross scatter radiation, a desired signal to noise ratio, a gating signal such as from a heart monitoring device, and/or other technique. Interpolation or the like can be used to generate additional cross scatter samples from the detected samples in order to derive scatter correction signals for each frame.

The medical imaging system 10 includes a scanner 12 having N x-ray sources $14_1$, $14_N$ (collectively referred to herein as x-ray sources 14), wherein N is an integer greater than one. The x-ray sources 14 are positioned at an angular offset (e.g., 60, 90, 120, etc. degrees) with respect to each other within an axial or transverse plane 16 and orthogonal to a longitudinal or z-axis 18. In one instance, the x-ray sources 14 are disposed about a rotating gantry 20. Rotating the gantry 20 about an imaging region 22 rotates the x-ray sources 14 about the imaging region 22. In another instance, the x-ray sources 14 are rotated about the imaging region 22 via other techniques such as electronically deflecting an e-beam. During scanning, the x-ray sources 14 can be concurrently driven throughout at least a portion of a data acquisition cycle such that the x-ray sources 14 simultaneously emit radiation through the imaging region 22.

The scanner 12 further includes N sets of detectors $24_1$, $24_N$ (collectively referred to herein as detectors 24). Each set of the detectors 24 subtends an angular arc opposite one of the x-ray sources 14 to define the imaging region 22 therebetween. In one instance, each detector within each set of detectors 24 rotates with and corresponds to a particular one of the x-ray sources 14 (e.g., with a third generation system). In another instance, the detectors within each set of detectors 24 reside at angular locations and, at any moment in time, are determined by the angular position of the x-ray source 14 (e.g., with a fourth generation system). Each detector within each set of detectors 24 detects radiation from actively emitting x-ray sources 14. A support 26 supports a subject, such as a human, within the imaging region 22. The support 26 may be movable in order to guide the subject to a suitable location within the imaging region 22 before, during and/or after performing a helical, axial, and/or other scan, for example, by moving the support 26 along the z-axis 18 and/or one or more other axes.

A control component 28 controls each of the x-ray sources 14. In one instance, such control includes concurrently turning one or more of the x-ray sources 14 "on" or "off." When all of the x-rays sources 14 are concurrently turned "on," each of the x-ray sources 14 concurrently emits radiation such that all of the x-ray sources 14 simultaneously emit radiation through the imaging region 22. As a result, each detector detects primary radiation from a corresponding one of the x-ray sources 14 and cross scatter radiation from the other x-ray sources 14 and generates a signal indicative of the detected primary and cross scatter radiation (projection data). By additionally detecting only cross scatter radiation (no primary radiation) at each detector, a scatter correction signal can be generated for each detector and used to scatter correct the projection data over one or more frames to substantially remove the cross scatter contributions therefrom.

In one instance, cross scatter radiation is detected with one or more detectors within a set of the detectors 24 by temporarily turning "off" the x-ray source 14 emitting primary radiation for that set of detectors 24 such that only the radiation emitted by the other x-ray sources 14 is detected by that set of detectors 24. This can be performed for one or more of the other x-ray sources 14 to obtain cross scatter data for one or more detectors in each set of detectors 24. When using this technique with a dual x-ray source configuration, primary only radiation can be detected by the detectors 24 corresponding to the x-ray source 14 emitting radiation while cross scatter radiation is detected by the other detectors 24. In another approach, cross scatter radiation can be detected by turning "off" all but one of the x-rays sources 14 and detecting the cross scatter contribution from that x-ray source 14 with the detectors 24 paired with the other x-ray sources 14. The detectors 24 corresponding to the radiation emitting x-ray source 14 can concurrently detect primary radiation. By alternating which of the x-ray sources 14 is emitting radiation, cross scatter contributions from each of the x-ray sources 14 can be detected by each of the detectors and primary radiation can be detected by each of the detectors 24. The resulting primary only signal can be used to refine the scatter correction technique (as described in detail below), for example, by comparing scatter corrected data with the clean or scatter free primary signal to determine whether a suitable scatter correction is being performed. In addition, the primary signal can be used to derive cross scatter contributions by subtracting the primary signal from the signal having both primary and cross scatter contributions.

Typically, cross scatter radiation varies slowly over angular position relative to primary radiation. As a result, cross scatter sampling can be angularly spaced, homogeneously or non-homogeneously, over a plurality of frames within each data acquisition cycle such that the x-rays sources 14 simultaneously emit radiation throughout one or more of the frames. Techniques such as interpolation or the like can be used to generate data points between the sampled frames. Various techniques can be used to determine the angular frequency at which cross scatter radiation is detected during data acquisition.

In one instance, an analysis component 30 is used to determine how often cross scatter is sampled. For example, the x-ray sources 14 can be driven such that only cross scatter radiation is detected by one or more of the sets of detectors 24 (e.g., by performing phantom measurements). The resulting cross scatter information can be provided to the analysis component 30, which can measure the rate at which the cross scatter radiation change over angular position. Cross scatter sampling can be set based on this rate in order to capture enough samples to generate scatter correction signals. In another instance, this rate is provided to the analysis component 30.

The angular cross scatter sampling spacing can be adjusted to more efficiently use the x-ray sources 14 such that they simultaneously emit radiation for a relatively large percentage of frames throughout each data acquisition cycle and minimize the amount of time in which the x-ray sources 14 are not simultaneously emitting radiation. As a result, statistics can be improved and noise can be reduced. By using a combination of the cross scatter rate of change and resulting statistics, the system can be optimized to achieve a desired balance between the performance of the scatter correction, statistics, and efficient use of the x-ray sources 14.

By way of non-limiting example, assume that the cross scatter angular sampling is determined as a function of the cross scatter radiation angular frequency and/or desired statistics. Also assume that this results in cross scatter being detected every 9 angular degrees. In between sampling, the x-ray sources 14 are concurrently emitting radiation. Over 90 degrees, this results in 10 cross scatter measurements, wherein at least one of the x-ray sources 14 is not emitting radiation. Assuming 250 frames (or views) along 90 degrees during a data acquisition cycle, the x-rays sources 14 simultaneously emit radiation for about 96% of the time. The angular cross scatter sampling spacing can be increased or decreased, depending on the results of the scatter correction and/or the statistics. By balancing the relative percentage of time that the x-ray sources 14 are simultaneously emitting radiation with acquiring enough information to derive suitable cross scatter signals, the number of photons detected can be increased to improve statistics and the data can be suitably scatter corrected for reconstruction.

In another instance, a component can provide a trigger signal to indicate when cross scatter is sampled. For example, with prospective gated cardiac CT applications, a device 32 (e.g., an ECG/EKG) that measures the electrical activity or motion state of the heart can be used to determine the sampling intervals for cross scatter for each detector. For instance, by monitoring the electrical activity of the heart while scanning a subject, the x-ray sources 14 can be gated such that cross scatter radiation is detected between the cardiac phases in which projection data is detected. Since projection data is not being detected during these in between phases, the angular sampling can be increased or decreased to acquire enough sampling to generate a scatter correction signal without affecting the statistic of the projection data. The sampling rate can also be based on patient dose since a higher sampling rate will result in greater patient dose assuming tube power remains the same. If desired, cross scatter radiation can also be detected during the cardiac phases through the techniques described herein. Such samples along with the samples collected in between the cardiac phases can be used to derive the scatter correction signal. As described above, interpolation or other techniques can be used to generate samples from the detected samples where desired.

The analysis component 30 can also monitor the results of the cross scatter correction and change the angular sampling to increase or decrease cross scatter sampling during each data acquisition cycle. As discussed above, by variously turning "off" one or more of the x-ray sources 14, primary radiation (without cross scatter radiation) can be detected by the detectors 24 corresponding to the x-ray source 14 emitting radiation while cross scatter radiation from this x-ray source 14 is detected by the other detectors 24. The resulting primary radiation signal, along with scatter corrected signals, can be provided to a correction verification component 34, which compares cross scatter corrected data points with corresponding primary signal data points. In one instance, if this difference falls outside a desired range and it is determined that the difference is a function of cross scatter sampling, the analysis component 30 can increase the angular sampling for each data acquisition cycle. Such increase may result in a signal more representative of the actual cross scatter contributions and, thus, a better scatter correction. In another instance, as long as this difference lies within a desired range, the analysis component 30 can vary the sampling in order to detect more photons and improve statistics, while maintaining a suitable scatter correction. The increase or decrease in the cross scatter sampling can be determined through an iterative approach by making an initial guess and adjusting the guess after each iteration to converge to a desired goal or automatically based on decisions facilitated by machine learning and the like. Such determination and adjustments can be performed before and/or during scanning the subject.

In another embodiment, a series of scatter measurements is performed on phantoms corresponding to different organs or regions of the body and/or for the intended acquisition protocols. In one instance, the cross scatter function can be measured for each detector for each scanning procedure by introducing a respective phantom into the scanner and performing n scatter measurement scans (one for each of the n detectors) for each procedure. In another instance, the cross scatter function can be measured for each detector for each scanning procedure by performing comprehensive scatter simulations of the respective scanner geometry and the phantoms with Monte-Carlo or other methods. Based on these cross scatter functions, an optimum sampling for each procedure can be determined. This information can be used by the control component 28, which can select the optimum scatter sampling for a chosen procedure. It is to be appreciated that this can provide an approximate scatter function for each procedure for deriving a suitable optimization of the scatter sampling for each procedure.

As described above, the control component 28 controls the x-ray sources 14 such that each detector concurrently detects primary and cross scatter radiation when multiple x-ray sources 14 are emitting radiation (e.g., over a relatively large percentage of each data acquisition cycle), detects solely primary radiation when only a corresponding one of the x-ray sources 14 is emitting radiation, and detects solely cross scatter radiation when the corresponding x-ray source 14 is not emitting radiation. As a result, the projection data includes data points that do not have a primary radiation contribution. These signals can be provided to an interpolation component 36, which interpolates the data to generate data points that include both primary and cross scatter contributions. The signals indicative of solely cross scatter radiation include cross scatter samples that are angularly spaced based on the angular sampling described above. As such, cross scatter samples are not obtained for all frames. These signals are also provided to the interpolation component 36, which interpolates the detected samples to generate samples to create a scatter signal with samples corresponding to a desired number of views or frames. Suitable interpolation techniques include linear, polynomial, spline, etc. interpolation.

The interpolated signals are provided to a correction component 38 that scatter-corrects the signals having primary and cross scatter contributions with the scatter correction signals. In one instance, a subtraction algorithm 40 is used to subtract the scatter correction signals from the signal having contributions of both primary and cross signals to substantially remove the cross scatter and render primary radiation signals. As there are also data samples of purely primary radiation, these data samples can be used to improve and/or assess the quality of the scatter correction. It is to be appreciated that the resulting scatter correction signals can be used to correct projection data independent of the numbers of slices. Thus, in one instance, although the cross scatter radiation scales with the number of slices, the scatter correction is not compromised as the number of slices increases. The scatter corrected signals are provided to a reconstruction system 42 that reconstructs the primary signals to generate volumetric data indicative of the scanned region of the subject. An image processor 44 processes the volumetric image data generated by the reconstruction system 42. The generated images can then be displayed, filmed, archived, forwarded to a treating clinician (e.g., emailed, etc.), fused with images from other imaging modalities, further processed (e.g., via measurement and/or visualization utilities and/or a dedicated visualization system), stored, etc.

A computing system (or console) 46 facilitates operator interaction with and/or control of the scanner 12. Software applications executed by the computing system 46 allow the operator to configure and/or control operation of the scanner 12. For instance, the operator can interact with the computing system 46 to select acquisition schemes, scan protocols, initiate, pause and terminate scanning, view images, manipulating volumetric image data, measure various characteristics of the data (e.g., CT number, noise, etc.), etc. Examples of suitable acquisition schemes, include, but are not limited to, 180 degree axial data acquisitions in which data is detected over 180 degrees plus a fan angle, helical scans, and multi-cycle gated axial scans. The computing system 46 communicates various information to the control component 28, including, but not limited to, instructions and/or parameters such as x-ray tube voltage, current, cross scatter angular sampling, interpolation algorithms, etc. The control component 28 uses such information as described above to control the scanner 12.

Figure 2:
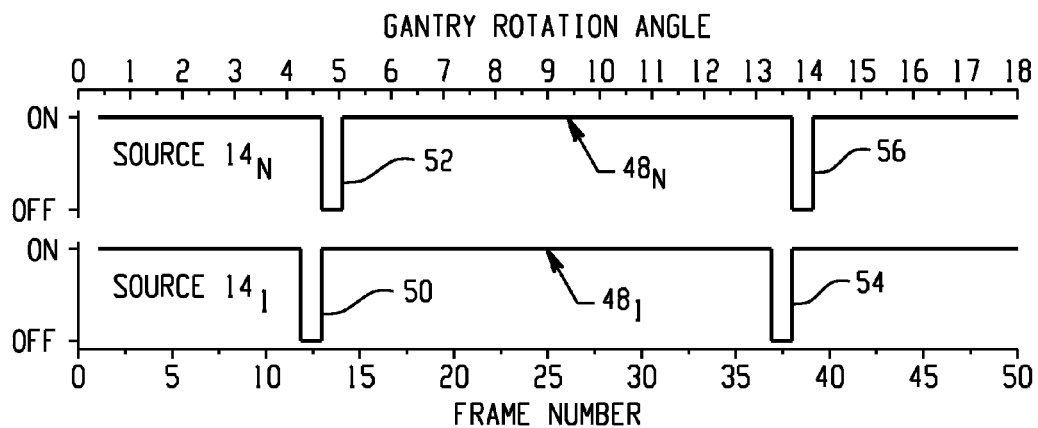
FIG. 2 illustrates exemplary x-ray source driving patterns for periodically sampling cross scatter radiation.

FIG. 2 illustrates exemplary x-ray source driving patterns as a function of gantry rotation angle and frame number for periodically sampling cross scatter radiation in connection with the imaging system 10. For brevity and clarity, only two such patterns are shown. A driving pattern $48_1$ activates the x-ray source $14_1$ to emit radiation, and the emitted radiation is detected with the corresponding detectors $24_1$. Concurrently, a driving pattern $48_N$ activates the x-ray source $14_N$ to emit radiation, which is detected with the corresponding detectors $24_N$. Since both of the x-ray sources 14 are concurrently emitting radiation, each of the detectors 24 also detects radiation emitted by the other x-ray source 14 (cross scatter radiation). As a result, both detectors $24_1$ and $24_N$ detect primary and cross scatter radiation as long as the x-ray sources $14_1$ and $14_N$ concurrently emit radiation.

In a cross scatter sampling interval 50, the driving pattern $48_1$ deactivates the x-ray source $14_1$ such that it no longer emits radiation (or emits an insubstantial amount of radiation). During this interval, the set of detectors 24, detect cross scatter radiation associated with the x-ray source 14$_N$ and the detectors 24$_N$ detect primary radiation emitted by the x-ray source 14$_N$. Upon lapse of the cross scatter interval 50, the x-ray source 14$_1$ begins emitting radiation again. In a cross scatter interval 52, the driving pattern 48$_N$ deactivates the x-ray source 14$_N$. Since the x-ray source 14$_N$ is not emitting radiation during the cross scatter interval 52, the detectors 24$_N$ detect cross scatter radiation associated with the x-ray source 14$_1$ and the detectors 24$_1$ detect primary radiation associated with the x-ray source 14$_1$. Upon lapse of the cross scatter interval 54, the x-ray source 14$_N$ begins emitting radiation again. The cross scatter intervals 52, 54 can be consecutive, as depicted, or separated by an angular or frame spacing. Additional cross scatter intervals, including intervals 54, 56, can be performed to acquire more cross sampling data points.

As described above, the cross scatter sampling frequency can be set based on the cross scatter radiation rate of change over gantry angle, efficient utilization of the x-ray sources 14, and/or statistics. Additionally or alternatively, the angular sampling can be triggered off an ECG or other signal. In this example, the cross scatter sampling associated with each of the x-ray sources 14 is about 9 angular degrees or about 20 frames. It is to be appreciated that cross scatter sampling intervals can be homogeneously or non-homogeneously spaced throughout a data acquisition cycle.

It is to be appreciated that measuring cross scatter by rough sampling the scatter measurements during the scan or using non-interesting heart phases in a cardiac scan for scatter measurements can also be used with systems with at least two x-ray sources and at least one detector for each source, where the foci of the sources are located at different z-positions.

Figure 3:
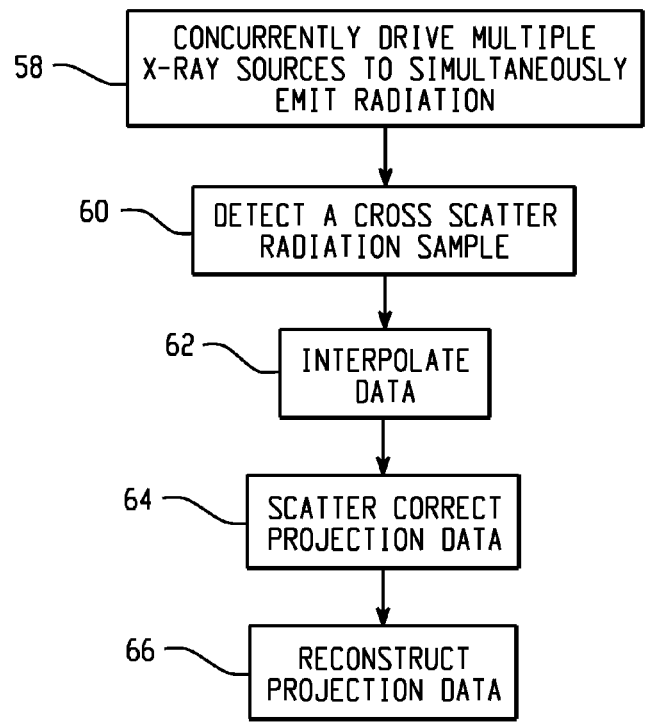
FIG. 3 illustrates an exemplary method for generating scatter correction signals for a medical imaging system that concurrently employs multiple x-ray sources to simultaneously irradiate a subject.

FIG. 3 illustrates a non-limiting method for scanning a subject with the medical imaging system. At reference numeral 58, two or more of the x-ray sources 14 are concurrently activated to simultaneously emit radiation through the imaging region 22. At 60, cross scatter radiation is detected by a least one of the sets of the detectors 24. As described above, this can be achieved by selectively turning off one of the x-ray sources 24 such that it corresponding set of detectors 24 detect cross scatter radiation emitted by the other x-ray sources. This can be repeated for each set of the detectors 24 in order to acquire cross scatter samples for each detector.

The frequency at which such samples are acquired can be determined through various approaches such as those described herein. For example, in one approach the angular sampling frequency can be set based on the frequency at which the cross scatter radiation angularly changes. Additionally or alternatively, the angular sampling frequency is set to efficiently drive the x-ray sources 14 such that they simultaneously emit radiation for a relatively large percentage of the data acquisition time. Additionally or alternatively, the angular sampling frequency can be set to improve statistics. Additionally or alternatively, the angular sampling can be triggered by a signal (e.g., an ECG signal).

At 62, the projection data and the data indicative of solely cross scatter radiation are interpolated to generate data points for views in which corresponding data was not collected. For instance, the interpolation component 36 interpolates the detected samples to generate data points during the intervals in which cross scatter was not detected. At 64, the interpolated signals are provided to the correction component 38, which scatter-corrects the signals having primary and cross scatter contributions with the scatter correction signals. Various scatter correction techniques, such as subtraction, can be used. At 66, the scatter corrected signals are reconstructed by the reconstruction system 42 to generate volumetric data indicative of the scanned region of the subject. The volumetric image can be displayed, filmed, archived, forwarded, fused with images from other imaging modalities, further processed, stored, etc.

The systems and/or methods described herein and/or derivations thereof can be used in connection with applications such as, but not limited to, cardiac CT, high temporal resolution scans, as well as other applications using multiple x-ray sources.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A computed tomography reconstruction method comprising:
   concurrently emitting radiation from at least two x-ray sources rotating about an imaging region through the imaging region and detecting with corresponding sets of detectors projection data, which includes primary radiation emitted by a corresponding one of the at least two x-ray sources and cross scatter radiation emitted by the other of the at least two x-ray sources;
   switching the output state of each of the at least two x-ray sources within a plurality of respective cross scatter sampling intervals and detecting with a corresponding one of the sets of detectors cross scatter radiation emitted by the other at least two x-ray sources, wherein the cross scatter sampling intervals are angularly spaced over a plurality of frames to allow the at least two x-ray sources to concurrently emit radiation throughout at least one frame;
   deriving scatter correction data for each set of detectors from corresponding cross scatter samples;
   scatter correcting the projection data with corresponding scatter correction data; and
   reconstructing the scatter corrected projection data to generate at least one image.

2. The method of claim 1, further including interpolating the cross scatter samples to generate cross scatter samples for frames in between the sampled frames.

3. The method of claim 1, further including:
   determining an angular frequency at which the cross scatter radiation varies with rotation angle; and
   computing the cross scatter sampling angular spacing as a function of the cross scatter angular frequency.

4. The method of claim 3, further including:
   determining image radiation statistics; and
   adjusting the cross scatter sampling angular spacing to achieve desired statistics.

5. The method of claim 4, wherein the statistics include a signal to noise ratio.

6. The method of claim 1, further including optimizing the angular spacing of the cross scatter sampling by balancing simultaneously emitting radiation for a relatively high percentage of the data acquisition time with acquiring cross scatter samples to derive cross scatter signals to scatter correct the projection data for reconstruction.

7. The method of claim 6, wherein the angular sampling spacing is based on simultaneously emitting radiation for more than 90% of a data acquisition cycle.

8. The method of claim 1, further including using a trigger signal to determine when a cross scatter sampled is detected.

9. The method of claim 8, wherein the trigger signal corresponds to the electrical activity of the heart.

10. The method of claim 1, further including gating acquisition of the cross scatter signal with a concurrently obtained ECG of a subject heart being scanned during a cardiac CT scan.

11. The method of claim 10, wherein the gating triggers the cross scatter sampling to occur in between cardiac phases in which projection data is detected.

12. The method of claim 1, wherein the angular spacing for the cross scatter sampling is one of homogenous and non-homogenous throughout a data acquisition cycle.

13. The method of claim 1, further including:
detecting primary radiation samples when only one of the x-ray sources is emitting radiation; and
comparing the primary radiation samples with scatter corrected projection samples to determine a performance of the scalier correction.

14. The method of claim 1, further including employing a data acquisition scheme including at least one of a 180 degree axial acquisition in which data is detected over 180 degrees plus a fan angle, a multi-cycle gated axial scan, and a helical scans.

15. A computed tomographic system comprising:
at least two x-ray sources that rotate about and concurrently emit radiation through an imaging region, wherein each of the at least two x-ray sources is deactivated within respective cross scatter sampling intervals in which cross scatter radiation for the deactivated x-ray source is sampled with an angular sampling spacing to allow the at least two x-ray sources to concurrently emit radiation throughout at least one data acquisition frame;
at least one detector for each of the at least two x-ray sources, wherein the at least one detector detects projection data when the at least two x-ray sources simultaneously emit radiation and cross scatter radiation for the deactivated x-ray source;
an interpolator that creates scatter correction samples from the detected cross scatter samples to generate samples for frames in between the sampled frames;
a correction component that scatter correct projection data with corresponding scatter correction data; and
a reconstruction system that reconstructs the scatter corrected projection data to generate at least one image.

16. The system of claim 15, wherein the at least two x-ray sources to concurrently emit radiation throughout at least two consecutive data acquisition frames.

17. The system of claim 15, wherein the angular cross scatter sampling spacing is a function of a cross scatter angular frequency.

18. The system of claim 17, wherein the angular cross scatter sampling spacing is further a function of at least one of imaging statistics and x-ray source efficiency.

19. The system of claim 15, further including a device that controls the cross scatter radiation sampling to acquire cross scatter samples during cardiac phases in which projection data is not detected.

20. The system of claim 15, wherein the angular spacing for the cross scatter sampling is one of homogenous and non-homogenous throughout a data acquisition cycle.

21. The system of claim 15, wherein the least one detector for each of the at least two x-ray sources further detects primary radiation samples when only a corresponding one of the x-ray sources emits radiation.

22. The system of claim 21, wherein the primary radiation samples are used to refine the scatter correction.

23. The system of claim 22, wherein the radiation is acquired during at least one of a 180 degree axial acquisition in which data is detected over 180 degrees plus a fan angle, a multi-cycle gated axial scan, and a helical scans.

24. The system of claim 15, wherein the scatter correction is independent of a width of a volume irradiated within the imaging region.

25. The system of claim 15, wherein the detectors are cone beam detectors.

26. The system of claim 15, wherein the x-ray sources are positioned at an angular offset with respect to each other within a rotating plane.

27. The system of claim 15, wherein the foci of the x-ray sources are located at two different positions along a z-axis.

28. A CT imaging system comprising:
means for concurrently emitting radiation through an imaging region with at least two x-ray sources;
means for selectively turning each of the at least two x-ray sources off during respective cross scatter sampling intervals and sampling cross scatter radiation for the deactivated x-ray source with an angular sampling spacing to allow the at least two x-ray sources to concurrently emit radiation throughout at least one data acquisition flame;
means for detecting radiation emitted by the at least two or more x-ray sources;
means for creating scatter correction signals from the detected cross scatter samples for a desired number of frames;
means for scatter correcting projection data with the scatter correction data; and
means for reconstructing the scatter corrected projection data to generate at least one image.

* * * * *